United States Patent [19]

Marion et al.

[11] Patent Number: 6,028,239
[45] Date of Patent: Feb. 22, 2000

[54] PROCESS FOR THE PRODUCTION OF TERTIARY OLEFIN(S) BY DECOMPOSITION OF THE CORRESPONDING ETHER USING A PARTICULAR CATALYST

[75] Inventors: Marie-Claire Marion, Villeurbanne; Alain Forestiere; Armand Barret, both of Vernaison, all of France

[73] Assignee: Institut Francais du Petrole, Rueil Malmaison, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/835,529

[22] Filed: Apr. 8, 1997

[30] Foreign Application Priority Data

Apr. 9, 1996 [FR] France .................................. 96 04418

[51] Int. Cl.$^7$ ....................................................... C07C 1/20
[52] U.S. Cl. ............................................. 585/640; 585/639
[58] Field of Search ..................................... 585/639, 640

[56] References Cited

U.S. PATENT DOCUMENTS

| 4,656,016 | 4/1987 | Taramasso et al. ..................... 423/277 |
| 5,095,164 | 3/1992 | Gabel et al. ............................. 585/640 |
| 5,354,831 | 10/1994 | Panster et al. ............................. 528/9 |

FOREIGN PATENT DOCUMENTS

| 2 669 021 | 5/1992 | France . |
| 35 09 292 | 12/1985 | Germany . |
| 2 188 853 | 10/1987 | United Kingdom . |

*Primary Examiner*—Bekir L. Yildirim
*Attorney, Agent, or Firm*—Millen, White, Zelano & Branigan, P.C.

[57] ABSTRACT

The invention concerns a process for the decomposition of tertiary alkyl ether(s), preferably selected from the group formed by ETBE, MTBE, TAME and ETAE, for the production of generally high purity tertiary olefin(s), preferably isobutene and isoamylenes, using a catalyst comprising at least one inorganic solid, for example a polysiloxane type solid, grafted with at least one alkyl sulphonic acid, aryl sulphonic acid or alkylaryl sulphonic acid type organic group.

25 Claims, No Drawings

PROCESS FOR THE PRODUCTION OF TERTIARY OLEFIN(S) BY DECOMPOSITION OF THE CORRESPONDING ETHER USING A PARTICULAR CATALYST

FIELD OF THE INVENTION

The invention concerns a process for the decomposition of tertiary alkyl ether(s) for the production of high purity tertiary olefin(s), characterised by the use of a catalyst comprising at least one inorganic solid, for example a polysiloxane type solid, grafted with at least one alkyl sulphonic acid, aryl sulphonic acid or alkylaryl sulphonic acid type organic group.

BACKGROUND OF THE INVENTION

Olefins with a tertiary carbon atom which forms part of a double bond undergo selective addition with alcohols to form tertioalkyl ethers. Such addition is an exothermic process and is catalysed by acids in general. Such reactions are used in the synthesis of high octane number oxygen-containing products such as MTBE (Methyl Tertio Butyl Ether), ETBE (Ethyl Tertio Butyl Ether), TAiME (Tertio Amyl Ether), or ETAE (Ethyl Tertio Amyl Ether). TAME and ETAE are obtained from a mixture containing two isoamylenes, 2-methyl-1-butene and 2-methyl-2-butene (3-methyl-1-butene is only slightly reactive). The selectivity of such ether synthesis reactions can also be exploited to separate tertiary olefins from the hydrocarbons which contain them. Separation of certain olefins from each other, for example the separation of isobutene and 1-butene, is difficult using a conventional distillation process. In contrast, separation of a tertiary alkyl ether (which is selectively produced) from the hydrocarbon cut from which it is produced is generally easy. Once isolated, the ether can be decomposed again to form the starting tertiary olefin and the alcohol employed. This is an endothermic process, in the presence of a generally acid catalyst and at a temperature which is higher than that used for synthesis. The tertiary olefin produced can thus be of high purity, depending on the optimised conditions.

Compared with other methods for the production of high purity tertiary olefins, such as those using isomerisation reactions, in processes using reactive distillation (for example isobutene:butene separation by transforming 1-butene into 2-butene), the scheme which incorporates synthesis then decomposition of the ether benefits from any infrastructure relating to the increasing importance of ethers in reformulated gasoline. Many refineries throughout the world have pure ether production plants, for example for the production of MTBE.

A large amount of pure ethers such as MTBE is already available on the international market. This means that the production of high purity tertiary olefin, for example isobutene, from ether, for example MTBE, can easily be carried out throughout the world, including locations remote from the refineries where such ethers are generally produced.

The exploitation of the selectivity of tertio alkyl ether decomposition reactions to the corresponding tertiary olefins has long been known, as shown, for example, in European patent application EP-A-0 068 785 (Sumitomo), and a variety of acidic solids have been described as catalysts for these reactions. Thus, French patent application FR-A-2 291 958 (Snamprogetti) describes the use of salts, oxides or complexes of tetravalent uranium, which can be supported on an alpha alumina, for example, with Lewis acidity.

United States patent U.S. Pat. No. 4,656,016 (Snamprogetti) describes the use of silica modified by the introduction of boron into its framework and, optionally, by cations ($H^+$, $NH_4^+$ or a metal cation). International patent application WO-A-91/01804 (EXXON) describes the use of clay (montmorillonite, kaolinite, attapulgite, bentonite . . .). Finally, U.S. Pat. No. 5,095,164 describes the use of ion exchange resins, for example sulphonated styrene-divinylbenzene resins (which are also generally used in tertio alkyl ether synthesis processes). Amberlyst 15 from Rohm & Haas or M-31 resin sold by Dow Chemical can be cited in this respect.

One of the major disadvantages of the resins cited above is that it is impossible to use them at high temperatures, more precisely above 120° C. At high temperatures, such resins de-sulphonate and thus lose their activity and/or acidity. Further, ether decomposition reactions are endothermic; thus the higher the temperature, the further the thermodynamic equilibrium of the reaction is displaced towards production of the olefin. An operating temperature limited to 120° C. results in low ether conversion which is also limited by the laws of thermodynamics.

U.S. Pat. No. 5,095,164 describes a process for the decomposition of tertio-alkyl ethers in the presence, for example, of macroporous sulphonated styrene-divinylbenzene resins using a distillation apparatus. The catalyst is placed at the bottom of a column which operates between 50° C. and 100° C., preferably between 60° C. and 80° C. The thermodynamic equilibrium of the decomposition reaction, which is poorly positioned because of the low operating temperature, is displaced by elimination of the reaction products (tertiary olefin and corresponding alcohol) by distillation. However, such a process has problems in product purification. In particular, it uses large quantities of water to recover the alcohol. Further, the unconverted ether is recovered from the bottom of the column with non negligible quantities of alcohol. It must therefore be purified before recycling to the process.

Other catalytic solids, for example those based on alumina, silica or silica-alumina, require the addition of water to improve alcohol recovery, and avoid the secondary reaction of the formation of the corresponding dialkyl ether, which in the case of methanol is:

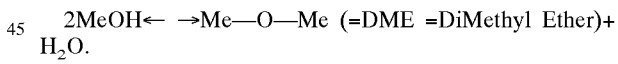

This has been described, for example, in United Kingdom patent application GB-A-1 165 479 (Shell) and in EP-A-0 589 557 (Sumitomo). However, the presence of water reduces the activity of the catalyst, by reducing its acidity (see, in particular, GB-A-1 165 479) and may require operating at a higher temperature, which can reduce the lifetime of the catalyst. Further, the presence of water induces a supplemental secondary reaction: the water reacts with the tertiary olefin produced to form an alcohol, such as in the case of the decomposition of MTBE (or ETBE): isobutene+$H_2O$→TBA (tertio Butyl Alcohol or 2-methyl-2-propanol). In that process, the yield of the desired tertiary olefin is observed to fall.

In general, the ether decomposition processes which are known to the skilled person use catalysts which have at least one of the following disadvantages: low activity, low selectivity, or low stability over time. Thus, for example, the process described by Exxon (application WO-A-91/01804), using a clay based catalyst, suggests a system which can regenerate the catalyst in situ. In addition, our application U.S. Pat. No. 5,171,920 can also be cited, which uses a catalyst based on silica modified by the addition of at least one element such as Li, Cs, Mg, Ca or La. Such solids are not very active due to a lack of acidity, and they have mediocre stability over time: the data given in Table 1 of Example 13 of that patent indicates that in 800 hours, the temperature must be increased by 50° C. to maintain constant the level of ether conversion.

SUMMARY OF THE INVENTION

The process of the invention can overcome the disadvantages cited above. Its novelty lies in using a catalyst comprising at least one inorganic solid, for example a polysiloxane type solid, grafted with at least one alkyl sulphonic acid, aryl sulphonic acid or alkylaryl sulphonic acid type organic group, the catalyst having a number of advantages.

The invention concerns a process for the decomposition of tertiary alkyl ether(s), preferably selected from the group formed by ETBE, NME, TAME and ETAE, for the production of generally high purity tertiary olefin(s), preferably isobutene or isoamylenes (2-methyl-1-butene and 2-methyl-2-butene), using a catalyst comprising at least one inorganic solid, for example and preferably a polysiloxane type solid, grafted with at least one alkyl sulphonic acid, aryl sulphonic acid or alkylaryl sulphonic acid type organic group.

A polysiloxane type solid grafted with at least one alkyl sulphonic acid, aryl sulphonic acid or alkylaryl sulphonic acid type organic group, comprised in the catalyst used in the process of the invention is sold, for example, by DEGUSSA under the trade name "DELOXAN". U.S. Pat. No. 4,552, 700, U.S. Pat. No. 5,354,831 and U.S. Pat. No. 5,380,791 describe the preparation of such a solid. These solids are strong Bronsted acids. The possibility of using such solids in ether decomposition reactions is just mentioned in the text of U.S. Pat. No. 5,354,831 (see column 9, lines 43 to 46), without being developed. One preferred implementation of the process of the invention is thus that the catalyst comprises DELOXAN.

The inorganic solid, preferably a polysiloxane type solid grafted with at least one alkyl sulphonic acid, aryl sulphonic acid or alkylaryl sulphonic acid type organic group comprised in the catalyst used in the process of the invention generally comprises at least one unit with the following formula (1):

$(O_{3/2}Si-R^1-SO_3)H^+$      (1)

where $R^1$ is an alkyl, aryl or alkylaryl radical.

Surprisingly, the process of the invention can result in greatly improved catalytic performances over prior art catalysts, and astonishingly, superior to those which could be envisaged from the three patents cited above.

Catalysts comprising at least one inorganic solid, for example a polysiloxane type solid, grafted with at least one alkyl sulphonic acid, aryl sulphonic acid or alkylaryl sulphonic acid type organic group, have numerous advantages during their use in the process of the invention.

One of the advantages of the process of the invention is that such catalysts are very active for the decomposition of tertioalkyl ethers to the corresponding tertiary olefins, compared with that currently described in the literature, meaning that a lower operating temperature can be used, for example 130° C., encouraging catalyst stability and also increasing the lifetime of the catalyst.

A further advantage of the process of the invention is that, because of the endothermicity of the reaction, and thus the favourable displacement of the thermodynamic equilibrium by a rise in temperature, the use of such catalysts generally means that a higher operating temperature (typically between 180° C. and 220° C.) can be used, although the use of such high temperatures is not obligatory in the present invention. The fact that the grafted solid is inorganic and not organic, for example a polysiloxane, means that such temperatures can be used without notable degradation of the catalyst. When using high temperatures in the process of the invention, the high activity of the catalysts used in the process of the present invention means that a high HSV (liquid hourly space velocity, expressed as the volume of liquid feed per volume of catalyst per hour) can be used. This reduces the catalytic volume required and also reduces the plant apparatus (doubling the economic advantage). Further, the possibility of using high throughputs (high HSV) reduces the number of secondary reactions: in the end, very good yields of olefin and alcohol are obtained.

A further advantage of the process of the invention is that such catalysts have excellent stability over time for the decomposition of tertioalkyl ethers to the corresponding tertiary olefin(s), which both facilitates operation and has a definite economic advantage, based on improvements such as less frequent down time and an overall saving on the cost of catalysts.

The operating conditions of the process of the invention are generally as follows. The (relative) pressure is generally in the range 1 to $10 \times 10^5$ Pa, preferably in the range 1 to $7 \times 10^5$ Pa. The use of such pressures generally means that simple cooling systems using water can be used to recover the olefin. In the particular preferred case, the production of isobutene from MTBE or ETBE, the pressure is generally in the range 5 to $10 \times 10^5$ Pa, preferably in the range 5 to $7 \times 10^5$ Pa. In the particular case of the production of isoamylenes (by decomposition of TAME or ETAE), the process pressure is generally in the range 1 to $5 \times 10^5$ Pa, preferably in the range 1 to $3 \times 10^5$ Pa. The temperature is generally in the range 100° C. to 250° C., preferably in the range 120° C. to 220° C., and more preferably in the range 160° C. to 220° C. The HSV, defined above, is generally in the range 0.5 to $200^{-1}$, preferably in the range 1 to $100^{-1}$, more precisely in the range 1 to 50 $h^{-1}$, and preferably in the range 2 to 25 $h^{-1}$; the HSV is a parameter which is generally directly linked to the operating temperature, such that the combination, inter alia, of these two parameters can optimise the product yield (optimal ether conversion, while maintaining good selectivities towards the products, the tertiary olefin and the alcohol, i.e. minimising secondary reactions, as is known to the skilled person).

The process of the invention is particularly suitable for the production of generally high purity tertiary olefins, with formula:

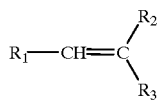

from corresponding ethers with formula:

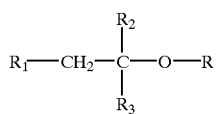

where $R^1$ is selected from the group formed by hydrogen, alkyl radicals, for example methyl, ethyl, n-propyl and isopropyl radicals, and R, $R^2$ and $R^3$, which may be identical or different, are each selected from the group formed by alkyl radicals, for example the methyl, ethyl, n-propyl and isopropyl radicals.

The primary alcohol (R—OH) recovered after decomposition of the ether preferably contains 1 to 6 carbon atoms per molecule.

The process of the invention is particular applicable to the decomposition of MTBE or ETBE to obtain high purity isobutene (and methanol or ethanol).

The process of the invention can also be applied to the decomposition of TAME or ETAE to produce high purity isoamylenes (and methanol or ethanol).

The process of the invention is generally carried out in at least one reaction zone comprising at least one reactor, each reactor operating either as a fixed bed, a mobile bed, or an expanded bed, or indeed a fluidised bed. The different operating modes of the reactor can be combined. Further, the reactor(s) of the reaction zone can operate in upflow or downflow mode, independently of each other when at least two reactors are present. The two circulation modes can be combined when the zone comprises at least two reactors, i.e., that at least one reactor operates in upflow mode and at least one reactor operates in downflow mode. It is also possible to use at least one radial type reactor.

The catalysts of the invention, comprising the catalytic solids described above, can be manufactured in different grain sizes. Thus DEGUSSA provides DELOXAN ASP

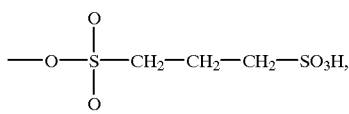

in two commercially available forms:

particle diameter: between 0.4 and 1.6 mm, for fixed bed applications;

particle diameter: 0.1 to 0.4 mm for suspended, expanded or fluidised operations.

However, any other particle size range can be envisaged within the context of the present invention, if it is suitable for the desired operation of the process of the invention. Preferably, the average equivalent diameter of the catalyst particles is generally in the range 0.1 to 10 mm.

The ether decomposition reaction is highly endothermic. It can thus lead to large temperature gradients in the reactor, which involves two major disadvantages:

a portion of the catalyst does not function under optimal thermal conditions.

Too low a temperature limits the catalytic activity, from both a kinetic and from a thermodynamic viewpoint;

there is a selectivity gradient to the reaction which can be difficult to control.

To limit the impact of the endothermicity of the reaction, the process of the invention can be carried out in a number of preferred implementations:

In one preferred implementation of the process of the invention, each reaction zone comprises at least one fixed bed reactor operating in upflow or downflow mode, and the reactor is preferably provided with means which can add heat to different regions inside the reactor. By way of non limiting example, a multitube reactor can be used such as that described on page 1311 of "Le Pétrole, Raffinage et Génie Chimique" [Oil: Refining and Chemical Engineering], vol II, by Pierre Wuithier (Editions TECHNIP). One advantage of this implementation is that the addition of heat to a portion or along the entire length of the reactor means that the temperature can be at least partially homogenised and the endothermic effect can be redressed. This technique is generally termed "near isothermal".

In a further preferred implementation of the process of the invention, at least one, preferably each reaction zone comprises at least two reactors disposed in series and provided with at least one intermediate heat exchange means to add heat at the inlet to at least one, preferably to each reactor and also, optionally, inside at least one, preferably each reactor (as indicated in the preceding implementation).

In a still further preferred implementation of the process of the invention, which may or may not be independent of the preceding implementation, each reaction zone comprises at least one reactor selected from mobile bed, expanded bed or fluidised bed reactors. One advantage of such an implementation is that the reactor at least partially improves thermal exchange and thus goes some way towards homogenising the temperature (i.e., reducing the temperature gradient and thus optimising the catalyst function). In a first variation of this implementation, the reactor comprises at least one means for recirculation (around the reactor(s) concerned). In a second variation of this implementation, the geometric shape is appropriate, i.e., so that the linear velocity can be high inside the reactor; in practice, this means that the reactor has a small diameter, for example. A combination of the two variations cited above can also be used. One advantage of re-circulation is good flexibility in the feed to be treated: the residence time (or linear velocity) in the reaction zone can be kept stable despite variations in the flow rate of the feed to be treated. As a consequence, such an implementation has at least two advantages, namely facility of operation of the process and better control of secondary reactions, due to complete control of the HSV, i.e., optimisation of the yields of both the tertiary olefin and of the alcohol.

In a yet still further implementation of the process of the invention, which may or may not be independent of the preceding implementations, at least one, preferably each reaction zone comprises at least two reactors in parallel, preferably 2 to 10, preferably provided with independent heating systems. One advantage of such an implementation is that the endothermic effect is then distributed in at least two reactors which leads to reactors in which the temperature gradients are smaller in each reactor. In this implementation, it is preferable, but not limiting, to use a fixed bed in each of the reactors in parallel, in upflow or downflow mode. A further advantage of such an implementation is great flexibility in the feed to be treated; depending on the quantity of feed to be treated, all or only a portion (or a certain number) of the parallel reactors can be supplied. The residence time in the reactor can thus be kept stable despite variations in flow rate of the feed to be treated. As a consequence, such an implementation includes at least two advantages, namely facility of operation of the process and better control of secondary reactions, i.e., optimisation of the yields of both tertiary olefin and of alcohol.

Whatever the implementation of the process of the invention, the process can comprise at least one recycling step for at least a portion of the effluent from the reaction zone to that reaction zone, to re-introduce at least a portion of the unreacted ether to the zone, after purification (i.e., elimination of the major portion of the reaction products, (i.e., tertiary olefin(s) and alcohol(s), and any secondary products, such as dimers).

Further, regardless of the implementation of the process of the invention, at least a portion of the effluent from the reaction zone can be directly incorporated into gasoline fractions, after elimination of the major portion of the principal reaction products (i.e., tertiary olefin(s) and alcohol(s).

In this case, the unreacted ether is incorporated into gasoline fractions without necessarily being freed of the major portion of the oligomers and other byproducts of the reaction. This is an economic advantage of the process of the invention.

In a still further implementation of the process of the invention, which may or may not be independent of the preceding implementations, conversion is limited in at least one reaction zone, then a finishing reaction is carried out in a reaction zone which can be limited to a single isolated downstream reactor.

The following examples illustrate the invention.

EXAMPLE 1

3 g of DELOXAN ASP catalyst with a grain size in the range 0.4 to 1.6 mm was introduced into a tubular reactor with a working volume of 10 ml. The reactor was provided with a double envelope in which a heat conducting fluid circulated to regulate the temperature. A mobile thermocouple in a sleeve was passed right through the reactor; this measured the temperature gradient in the reactor. The reactor was kept pressurised using an escape valve set at $7 \times 10^5$ Pa relative. The unit was provided with an in-line FID type chromatograph which could analyse all of the effluent directly. The reactor was supplied with a feed containing more than 96% by weight of MTBE. The results obtained are given in Table 1.

This example illustrates the high activity of the catalyst which means that high HSVs can be used, thus minimising secondary reactions which degrade the selectivities towards isobutene and methanol.

TABLE 1

| Temperature of heat conducting fluid (°C.) | HSV ($h^{-1}$) | Average temperature in reactor (°C.) | MTBE conversion (%) | Selectivity towards isobutene (%) | Selectivity towards methanol (%) |
|---|---|---|---|---|---|
| 130 | 4.3 | 121.1 | 63 | 96.7 | 98.8 |
| 160 | 24 | 121.0 | 64.5 | 99.7 | 99.9 |

EXAMPLE 2

1 g of DELOXAN ASP catalyst with a grain size in the range 0.4 to 1.6 mm was introduced into a tubular reactor with a working volume of 10 ml. The reactor was provided with a double envelope in which a heat conducting fluid circulated to regulate the temperature. A mobile thermocouple in a sleeve was passed right through the reactor; this measured the temperature gradient in the reactor. The reactor was kept pressurised using an escape valve set at $7 \times 10^5$ Pa relative. The unit was provided with an in-line FED type chromatograph which could analyse all of the effluent directly. The reactor was supplied with a feed containing more than 96% by weight of MTBE. The results obtained are given in Table 2.

In addition to the exceptional activity of the catalyst, this example shows the size of the endothermic effect, in particular when a high HSV is used.

TABLE 2

| Age of catalyst (h) | Temperature of heat conducting fluid T1 (°C.) | HSV ($h^{-1}$) | Average temperature in reactor T2 (°C.) | Average ΔT (T1–T2) (°C.) | MTBE conversion (%) |
|---|---|---|---|---|---|
| 85 | 160 | 6 | 148.1 | 11.9 | 83.2 |
| 110 | 180 | 6 | 165.7 | 14.3 | 91.6 |
| 190 | 180 | 13.5 | 149.2 | 30.8 | 88 |
| 220 | 180 | 23.5 | 143.5 | 36.5 | 74 |
| 245 | 200 | 8 | 178.9 | 21.1 | 95.4 |
| 270 | 200 | 13.5 | 163.5 | 36.5 | 92.6 |
| 310 | 200 | 23.5 | 158 | 42 | 82 |
| 390 | 220 | 8.5 | 200.9 | 19.1 | 97.5 |
| 420 | 220 | 13.5 | 182.8 | 37.2 | 96.5 |
| 450 | 220 | 23.5 | 174.4 | 45.6 | 92 |

EXAMPLE 3

This example illustrates the activity and also the stability of the catalyst. The apparatus and catalyst quantity were the same as in Example 1. The results are shown in Table 3.

| Age of catalyst (h) | Temperature of heat conducting fluid (°C.) | HSV ($h^{-1}$) | MTBE conversion (%) |
|---|---|---|---|
| 250 | 130 | 4.3 | 62 |
| 450 | 130 | 4.3 | 62 |
| 700 | 130 | 4.3 | 61 |
| 930 | 130 | 4.3 | 60.5 |
| 1010 | 180 | 4.3 | 93.4 |
| 1100 | 180 | 4.3 | 92.8 |
| 1250 | 180 | 4.3 | 92.5 |
| 1500 | 180 | 4.3 | 92.1 |
| 1750 | 180 | 4.3 | 92.0 |
| 2100 | 180 | 4.3 | 91.8 |

EXAMPLE 4 (comparative)

This example used a known prior art catalyst as described and claimed in U.S. Pat. No. 5,171,920. Both the activity and stability of the catalyst, used under the same conditions as those described for Example 3, were far poorer than those shown in Example 3.

Apart from the size of the reactor, the apparatus was the same as in Examples 1, 2 and 3.

67.2 g of $MgO/SiO_2$ type catalyst with a grain size in the range 2 to 3 mm, prepared according to the invention described in U.S. Pat. No. 5,171,920, was introduced into a tubular reactor with a working volume of 145 ml. The reactor was supplied with a feed containing 96% by weight of MTBE. The results obtained are shown in Table 4.

TABLE 4

| Age of catalyst (h) | Temperature of heat conducting fluid (°C.) | HSV ($h^{-1}$) | MTBE conversion (%) |
|---|---|---|---|
| 0 | 200 | 1 | 63 |
| 100 | 200 | 1 | 60 |
| 200 | 200 | 1 | 57 |
| 300 | 200 | 1 | 54 |
| 400 | 200 | 1 | 51 |

What is claimed is:

1. A process for the decomposition of tertiary alkyl ether(s) for the production of tertiary olefin(s), using a catalyst comprising at least one solid particulate polysiloxane grafted with at least one alkyl sulphonic acid, aryl sulphonic acid or alkyl aryl sulphonic acid type organic group, said process being conducted with an HSV, expressed as the volume of liquid feed per volume of catalyst per hour, in the range of 2–25 $h^{-1}$.

2. A process according to claim 1, in which the pressure is in the range 1 to $10 \times 10^5$ Pa, and the temperature is in the range of 100° C. to 250° C.

3. A process according to claim 1, in which the catalyst is used in at least one reaction zone comprising at least one reactor functioning as a fixed bed, mobile bed, expanded bed or a fluidised bed.

4. A process according to claim 3, in which the catalyst is used in at least one reaction zone comprising at least one reactor which functions in upflow or in downflow mode.

5. A process according to claim 4, in which said reactor is provided with means for adding heat to various regions inside the reactor.

6. A process according to claim 4, in which said reactor is a multitubular reactor.

7. A process according to claim 4, in which at least one reaction zone comprises two reactors disposed in series and provided with at least one intermediate heat exchange means for providing heat to the inlet to at least one reactor.

8. A process according to claim 7, in which said reactors are provided with at least one intermediate heat exchange means for providing heat to the inside of at least one reactor.

9. A process according to claim 1, in which at least one reaction zone comprises at least one reactor operating as a mobile bed, an expanded bed or a fluidised bed.

10. A process according to claim 9, in which said reactor comprises at least one recirculation means or such that each reactor has a geometric shape which is appropriate for operating as a mobile bed, expanded bed or fluidised bed.

11. A process according to claim 3, in which at least one reaction zone comprises at least two reactors in parallel.

12. A process according to claim 11, in which the reaction zone comprises 2 to 10 reactors in parallel.

13. A process according to claim 11, in which the reactors in parallel are provided with independent heating means.

14. A process according to claim 11, in which a portion of said reactors is supplied.

15. A process according to claim 2, comprising at least one recycling step for at least a portion of the effluent from one of the reaction zones to said reaction zone.

16. A process according to claim 2, in which at least a portion of the effluent from one of the reaction zones is directly incorporated into gasoline fractions.

17. A process according to claim 16, in which said incorporation is made after purification of the major portion of said effluent.

18. A process according to claim 1, in which the solid polysiloxane grafted with at least one alkyl sulphonic acid organic group comprised in the catalyst used in the process of the invention comprises at least one unit with the following formula (1):

where $R^1$ is an alkyl, aryl or alkylaryl radical.

19. A process according to claim 1, in which said catalyst comprises

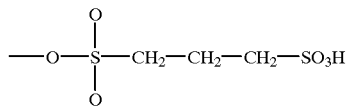

20. A process according to claim 1, for the decomposition of tertiary alkyl ether(s) selected from the group formed by ETBE and MTBE for the production of isobutene or from the group formed by TAME and ETAE for the formation of isoamylenes.

21. A process according to claim 18, wherein $R^1$ is alkyl.

22. A process according to claim 1 wherein the solid upon which said at least one alkyl sulphonic acid, aryl sulphonic acid or alkyl aryl sulphonic acid organic group, consists essentially of said polysiloxane.

23. A process according to claim 22 wherein said process comprises the decomposition of MTBE for the selective production of isobutene.

24. A process according to claim 1, wherein the grafted polysiloxane is in the form of particles having a particle size in the range of 0.1 to 10 mm.

25. A process according to claim 1, wherein the grafted particulate polysiloxane is unsupported.

* * * * *